United States Patent
Luo et al.

(10) Patent No.: US 9,823,205 B2
(45) Date of Patent: Nov. 21, 2017

(54) METHODS AND SYSTEMS FOR DETERMINING SURFACE RELAXIVITY OF A MEDIUM USING NUCLEAR MAGNETIC RESONANCE

(71) Applicant: SCHLUMBERGER TECHNOLOGY CORPORATION, Sugar Land, TX (US)

(72) Inventors: Zhixiang Luo, Chapel Hill, NC (US); Jeffrey Paulsen, Brookline, MA (US); Yi-Qiao Song, Newton Center, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 420 days.

(21) Appl. No.: 14/543,290

(22) Filed: Nov. 17, 2014

(65) Prior Publication Data

US 2016/0139066 A1    May 19, 2016

(51) Int. Cl.
*G01N 24/08*    (2006.01)
*G01R 33/44*    (2006.01)
*G01V 3/32*    (2006.01)

(52) U.S. Cl.
CPC ............ *G01N 24/081* (2013.01); *G01V 3/32* (2013.01); *G01R 33/448* (2013.01)

(58) Field of Classification Search
CPC ....... G01N 24/081; G01V 3/32; G01R 33/448
USPC ................................................. 324/300, 303
See application file for complete search history.

(56) References Cited

U.S. PATENT DOCUMENTS

| | | | |
|---|---|---|---|
| 5,796,252 | A | 8/1998 | Kleinberg et al. |
| 6,462,542 | B1 | 10/2002 | Venkataramanan et al. |
| 6,570,382 | B1 | 5/2003 | Hurlimann et al. |
| 6,883,702 | B2 | 4/2005 | Hurlimann et al. |
| 2013/0057277 | A1 | 3/2013 | Zielinski et al. |

(Continued)

FOREIGN PATENT DOCUMENTS

| | | |
|---|---|---|
| WO | 2011/091269 A2 | 7/2011 |
| WO | 2012144976 A1 | 10/2012 |

OTHER PUBLICATIONS

International Search Report for corresponding PCT Application Serial No. PCT/US2015/060862, dated Feb. 29, 2016, 3 pp.

(Continued)

*Primary Examiner* — Melissa Koval
*Assistant Examiner* — Rahul Maini

(57) ABSTRACT

Methods and systems for determining surface relaxivity from nuclear magnetic resonance measurements relate to applying multiple nuclear magnetic resonance (NMR) diffusion editing Carr-Purcell-Meiboom-Gill (CPMG) pulse sequences to the porous medium, wherein the diffusion editing CPMG pulse sequences have a diffusion encoding time $\Delta$; receiving NMR data generated by the pulse sequences; processing the received NMR data to obtain a distribution $f(T_2,D)$ for the diffusion encoding time $\Delta$; repeating the applying, the receiving, and the processing at least one time for pulse sequences having different respective diffusion encoding times $\Delta$ to obtain respective distributions $f(T_2,D)$ corresponding respectively to the different diffusion encoding times $\Delta$; and utilizing the respectively obtained distributions $f(T_2,D)$ to generate a surface relaxivity ($\rho$) determination.

45 Claims, 8 Drawing Sheets

(56) References Cited

U.S. PATENT DOCUMENTS

2013/0200890 A1  8/2013  Hursan
2014/0184220 A1  7/2014  Paulsen et al.

OTHER PUBLICATIONS

Casieri, et al, "Pore-siz Evaluation by Single-sided Nuclear Magnetic Resonance Measurements: Compensation of Water Self-Diffusion Effect on Transverse Relaxation," Journal of Applied Physic., 2005 vol. 97, No. 4, 043901, 10 pp.

Arns et al, "Numerical Analysis of Nuclear Magnetic Resonance Relaxation-Diffusion Responses of Sedimentary Rock," New Journal of Physics vol. 13 (2011) 015004, 17 pp.

Basan, et al., "Pore-size data in petrophysics: a perspective on the measurement of pore geometry", Geological Society, London, Special Publications, vol. 122, Issue: 1, 1997, pp. 47-67.

Borgia, et al., "Nuclear magnetic resonance relaxivity and surface-to-volume ratio in porous media with a wide distrubution of pore sizes", Journal of Applied Physics, vol. 79, 1996, pp. 3656-3664.

Brownstein, et al., "Importance of classical diffusion in NMR studies of water in biological cells", Phys. Rev. A., vol. 19, Jun. 1, 1979, pp. 2446-2453.

Hürlimann, et al., "Diffusion-relaxation distribution functions of sedimentary rocks in different saturation states", Magnetic Resonance Imaging, vol. 21, 2003, pp. 305-310.

Kleinberg, "Utility of NMR T2 distributions, connection with capillary pressure, clay effect, and determination of the surface relaxivity parameter p2", Magnetic Resonance Imaging, vol. 14, Issues 7-8, 1996, pp. 761-767.

Latour, et al., "Time-Dependent Diffusion Coefficient of Fluids in Porous Media as a Probe of Surface-to-Volume Ratio", Journal of Magnetic Resonance, Series A, vol. 101, Issue 3, Feb. 15, 1993, pp. 342-346.

Mitra, et al., "Diffusion propagator as a probe of the structure of porous media", Physical Review Letters, vol. 68, Jun. 15, 1992, pp. 3555-3558.

Mitra, et al., "Short-Time Behavior of the Diffusion Coefficient as a Geometrical Probe of Porous Media", Physical Review B, vol. 47, No. 14, Apr. 1, 1993, pp. 8565-8574.

Price, "Pulsed-field gradient nuclear magnetic resonance as a tool for studying translational diffusion, part 1: basic theory", Magnetic Resonance, vol. 9 Issue 5, 1997, pp. 299-336.

Song, et al., "T1-T2 Correlation Spectra Obtained Using a Fast Two-Dimensional Laplace", Journal of Magnetic Resonance, vol. 154, No. 2, Feb. 2002, pp. 261-268.

Venkataramanan, et al., "Solving Fredholm integrals of the first kind with tensor product structure in 2 and 2.5 dimensions", Signal Processing, IEEE Transactions, vol. 50, Issue: 5, May 2002, pp. 1017-1026.

Wilkinson, et al., "Nuclear magnetic relaxation in porous media: The role of the mean lifetime τ (ρ,D)", Physical Review B 44, Sep. 1, 1991, p. 4960.

Zielinski, et al., "Restricted Diffusion Effects in Saturation Estimates From 2D Diffusion-Relaxation NMR Maps", SPE 134841—SPE Annual Technical Conference and Exhibition, Florence, Italy, Sep. 19-22, 2010, 9 pages.

Quantitative Measurement of Two-Dimensional Distribution Functions of Diffusion and Relaxation in Grossly Inhomogeneous Fields, Journal of Magnetic Resonance 157, 31-42 (2002).

METHODS AND SYSTEMS FOR DETERMINING SURFACE RELAXIVITY OF A MEDIUM USING NUCLEAR MAGNETIC RESONANCE

TECHNICAL FIELD

The subject disclosure relates to the measurement of the properties of a medium such as rock. More particularly, the subject disclosure relates to methods for determining surface relaxivity of a medium using nuclear magnetic resonance. The subject disclosure has particular application to the hydrocarbon industry, although it is not limited thereto.

BACKGROUND

Nuclear magnetic resonance (NMR) is a useful tool in the determination of the pore size distribution (PSD) of a porous medium. The PSD of a medium can be determined by making relaxation measurements of a fluid saturating the medium. In particular, the $T_2$ spin-spin relaxation time is related to pore size according to $$\frac{1}{T_2} = \frac{1}{T_{2b}} + \rho \frac{S}{V},$$

where $T_{2b}$ is the $T_2$ value of the bulk fluid, $\rho$ is the surface relaxivity, and S/V is the surface volume ratio. See, e.g., Kleinberg, R., et al., "Utility of NMR $T_2$ distributions, connection with capillary pressure, clay effect, and determination of the surface relaxivity parameter $\rho_2$," Magnetic Resonance Imaging, Vol. 14 pp. 761-767 (1996)). The determination of surface relaxivity $\rho$ may be considered important for quantitative interpretation of NMR data. Surface relaxivity is usually determined by finding the value of $\rho$ that matches the PSD derived from the NMR $T_2$ distribution to the PSD of an independent laboratory measurement, for example via a capillary pressure measurement. See, e.g., Borgia, G., et al., "Nuclear magnetic resonance relaxivity and surface-to-volume ratio in porous media with a wide distribution of pore sizes," Journal of Applied Physics, Vol. 79 pp. 3656-3664 (1996); and Basan, P. B., et al., "Pore-size data in petrophysics: a perspective on the measurement of pore geometry," Geological Society, London, Special Publications, Vol. 122 pp. 47-67 (1997). However, an independent measurement of the surface area is not always available, such as in formation (borehole) logging applications where the medium remains in situ.

When water is located inside a porous medium, motion of the water is affected by the solid matrix of that medium. The corresponding effect on the apparent diffusion coefficient is well established both theoretically and experimentally and that effect may be utilized to probe the S/V information. See, Mitra, P. P., et al., "Diffusion propagator as a probe of the structure of porous media," Physical Review Letters, Vol. 68 pp. 3555-3558 (1992); and Latour, L. L., et al., "Time-dependent diffusion coefficient of fluids in porous media as a probe of surface-to-volume ratio," Journal of Magnetic Resonance, Series A, Vol. 101 pp. 342-346 (1993). Recently, a purely in-situ NMR logging approach that combines $T_2$ relaxation and diffusion measurements to determine surface relaxivity was proposed. See, Zielinski, L., et al., "Restricted Diffusion Effects in Saturation Estimates from 2D Diffusion-Relaxation NMR Maps," SPE Annual Technical Conference and Exhibition, 2010; and Zielinski, L., et al., "Method for Determining Rock Formation Fluid Interaction Properties Using Nuclear Magnetic Resonance Well Logging Measurements," U.S. Patent Publication #2013/0057277 (2013) which is hereby incorporated by reference herein in its entirety. An apparent advantage of using restricted diffusion to determine S/V is that $T_2$ relaxation is affected by paramagnetic centers on the surface through the diffusion process. See, Brownstein, K. R., and Tarr, C., "Importance of classicial diffusion in NMR studies of water in biological cells," Physical Review A, Vol. 19 p. 2446 (1979); Wilkinson, D. J., et al., "Nuclear magnetic relaxation in porous media: The role of the mean lifetime $\tau(\rho,D)$," Physical Review B, Vol. 44 p. 4960 (1991). Unlike systems that use one dimensional time dependent diffusion data to determine surface relaxivity, Zielinski et al. analyze a 2D diffusion-relaxation ($DT_2$) map which contains S/V information as function of pore size instead of the ratio of total surface to total volume ($S_T/V_T$).

Zielinski et al.'s methodology is suitable to homogenous (e.g., single pore size length scale) sample applications where $T_2$ differs notably from its bulk value. The methodology utilizes inputs to the analysis such as tortuosity, bulk diffusion coefficients, and a fixed heterogeneity length.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In accordance with example embodiments, a method of determining surface relaxivity of a porous medium includes: applying multiple nuclear magnetic resonance (NMR) diffusion editing Carr-Purcell-Meiboom-Gill (CPMG) pulse sequences to the porous medium, wherein the diffusion editing CPMG pulse sequences have a diffusion encoding time $\Delta$; receiving NMR data generated by the pulse sequences; processing the received NMR data to obtain a distribution $f(T_2,D)$ for the diffusion encoding time $\Delta$; repeating the applying, the receiving, and the processing at least one time for pulse sequences having different respective diffusion encoding times $\Delta$ to obtain respective distributions $f(T_2,D)$ corresponding respectively to the different diffusion encoding times $\Delta$; and utilizing the respectively obtained distributions $f(T_2,D)$ to generate a surface relaxivity ($\rho$) determination.

In accordance with example embodiments, a method of determining surface relaxivity of a porous medium includes: (a) generating multiple nuclear magnetic resonance (NMR) diffusion editing–CPMG (Carr-Purcell-Meiboom-Gill) pulse sequences with a diffusion encoding time $\Delta$ that interact with the porous medium, and acquiring resulting data; (b) processing the resulting data to obtain a distribution $f(T_2,D)$ for that $\Delta$; (c) calculating a mean diffusion coefficient $\overline{D}(T_{2s})$ for each $T_2$ value, where $T_{2s}$ is the transverse relaxation time due to surface relaxation; (d) calculating a $T_2$ distribution $g(T_{2s})$; (e) utilizing the calculated $T_2$ distribution and the calculated mean diffusion coefficient in order to generate a determination of surface relaxivity ($\rho$) by choosing values for the surface relaxivity and at least one parameter to cause a fitting function of the surface relaxivity and a parameter $\Gamma$ to closely approximate the average diffusion coefficient $\overline{D}(T_{2s})$, the fitting function is defined by $$\frac{D(\Delta, T_{2s})}{D_0} = 1 - (1-\alpha)\frac{\beta\frac{L_D}{\rho T_{2s}} + (1-\alpha)\left(\frac{L_D}{\Gamma\rho T_{2s}}\right)^2}{(1-\alpha) + \beta\frac{L_D}{\rho T_{2s}} + (1-\alpha)\left(\frac{L_D}{\Gamma\rho T_{2s}}\right)^2}$$

where $D_0$ is a bulk diffusion coefficient, $$D(\infty)/D_0, \beta = \frac{4}{9\sqrt{\pi}}, L_D = \sqrt{D_0\Delta}, \text{ and } \Gamma = L_M/\rho T_{2s},$$

where $L_M$ is a length scale characterizing a transition between a short-time and long-time diffusion limit.

In accordance with example embodiments, a method utilizing nuclear magnetic resonance (NMR) measurements to determine surface relaxivity of a porous medium includes: (a) generating multiple NMR diffusion editing pulse sequences for each of a plurality of diffusion encoding times $\Delta$ that interact with the porous medium, and acquiring resulting data; (b) processing the resulting data to obtain mean diffusion coefficient $\overline{D}(T_2)$ for each $T_2$ value of each of the plurality of encoding times $\Delta$, where $T_{2s}$ is the transverse relaxation time due to surface relaxation, and to obtain $T_2$ distributions $g(T_{2s})$; (c) utilizing respective calculated $T_2$ distributions and respective calculated mean diffusion coefficients in a data-fitting error minimization procedure in order to generate a determination of surface relaxivity ($\rho$), where the data-fitting error minimization procedure utilizes a fitting function with a parameter that permits the length scale characterizing the transition between the short-time and long-time diffusion limit ($L_M$) to scale with pore size.

In accordance with example embodiments, a method of determining surface relaxivity of a porous medium includes: (a) generating multiple nuclear magnetic resonance (NMR) diffusion editing pulse sequences for each of a plurality of diffusion encoding times $\Delta$ that interact with the porous medium, and acquiring resulting data; and (b) without utilizing non-NMR measurements, fitting a function relating the surface relaxivity to NMR diffusion coefficients and diffusion lengths to diffusion coefficients calculated from the resulting data in order to obtain a surface relaxivity determination for the porous medium.

In accordance with example embodiments, a nuclear magnetic resonance (NMR) system includes: a coil for applying a NMR pulse sequence to a substance; a NMR transmitter coupled to the coil; a processor; and a memory storing instructions executable by the processor to apply multiple nuclear magnetic resonance (NMR) diffusion editing Carr-Purcell-Meiboom-Gill (CPMG) pulse sequences to the porous medium, wherein the diffusion editing CPMG pulse sequences have a diffusion encoding time $\Delta$; receive NMR data generated by the pulse sequences; process the received NMR data to obtain a distribution $f(T_2,D)$ for the diffusion encoding time $\Delta$; repeat the applying, the receiving, and the processing at least one time for pulse sequences having different respective diffusion encoding times $\Delta$ to obtain respective distributions $f(T_2,D)$ corresponding respectively to the different diffusion encoding times $\Delta$; and utilize the respectively obtained distributions $f(T_2,D)$ to generate a surface relaxivity ($\rho$) determination.

Additional aspects, embodiments, objects and advantages of the disclosed methods may be understood with reference to the following detailed description taken in conjunction with the provided drawings.

DETAILED DESCRIPTION

Figure 1:
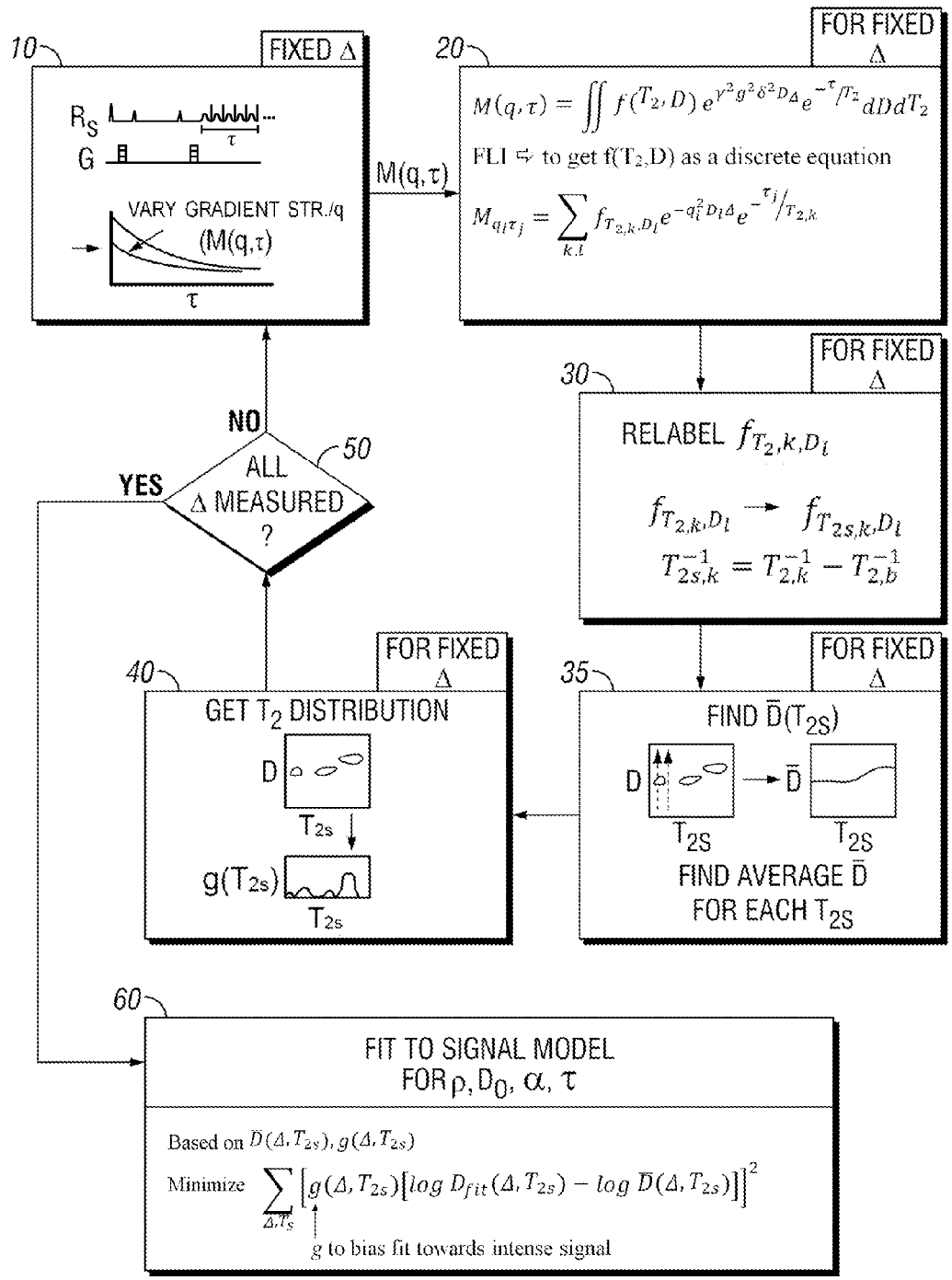
FIG. 1 is a flow chart of a method for determining the surface relaxivity of a medium.

Before turning to the drawings, an understanding is useful of some of the physics underlying hereinafter-described embodiments.

The time dependent diffusion coefficient in porous media depends on surface volume ratio S/V. See, e.g., Mitra, P. P. et al., "Diffusion propagator as a probe of the structure of porous media," Physical Review Letters, Vol. 68, pp. 3555-3558 (1992); and Mitra, P. P. et al., "Short-time behavior of the diffusion coefficient as a geometrical probe of porous media," Physical Review B, Vol. 47, p. 8565 (1993). In the short time limit, i.e. where the characteristic diffusion length ($\sqrt{2D_0\Delta}$) is much smaller than the pore size, the apparent diffusion coefficient decrease is proportional to S/V, described by $$\frac{D(\Delta)}{D_0} = 1 - \frac{4}{9\sqrt{\pi}}\frac{S}{V}\sqrt{D_0\Delta}, \qquad (1)$$

where $D_0$ is the bulk diffusion coefficient and $\Delta$ is the diffusion time. In the long time limit, $D(\Delta)$ approaches the asymptotic value $D(\infty)/D_0=\alpha$. A Padé approximation can be used to connect the two limits, $$\frac{D(\Delta)}{D_0} = 1 - (1-\alpha)\frac{\beta L_D\left(\frac{S}{V}\right) + (1-\alpha)\left(\frac{L_D}{L_M}\right)^2}{(1-\alpha) + \beta L_D\left(\frac{S}{V}\right) + (1-\alpha)\left(\frac{L_D}{L_M}\right)^2} \qquad (2)$$

Where $$\beta = \frac{4}{9\sqrt{\pi}}, L_D = \sqrt{D_0 \Delta},$$

and $L_M$ is the length scale characterizing the transition between the short-time and long-time diffusion limit. See, Latour, L. L., et al., "Time-dependent diffusion coefficient of fluids in porous media as a probe of surface-to-volume ratio," Journal of Magnetic Resonance, Series A, Vol. 101 pp. 342-346 (1993); and Hürlimann, M., et al., "Diffusion-relaxation distribution functions of sedimentary rocks in different saturation states," Magnetic Resonance Imaging, Vol. 21, pp. 305-310 (2003).

NMR $T_2$ relaxation time is also affected in porous media by the surface to volume ratio as described by the expression $$\frac{1}{T_{2s}} = \rho \frac{S}{V} \tag{3}$$

where $T_{2s}$ is the transverse relaxation time due to surface relaxation (where $$\frac{1}{T_{2s}} = \frac{1}{T_2} - \frac{1}{T_{2b}},$$

with $T_{2b}$ being the bulk relaxation) and $\rho$ is the surface relaxivity. Combining equations (2) and (3) leads to a formula relating $T_{2s}$ and $D(\Delta)$:

$$\frac{D(\Delta)}{D_0} = 1 - (1-\alpha)\frac{\beta\frac{L_D}{\rho T_{2s}} + (1-\alpha)\left(\frac{L_D}{L_M}\right)^2}{(1-\alpha) + \beta\frac{L_D}{\rho T_{2s}} + (1-\alpha)\left(\frac{L_D}{L_M}\right)^2} \tag{4}$$

It should be appreciated that the use of a single transition length $L_M$ in equation (4) causes equation (4) to be effective for uniform pore size samples but does not necessarily address the case of a wide pore size distribution such as in rock formations. It should also be appreciated that in cases involving very large pores and low surface relaxivity where $T_{2s}$ approaches infinity, equation (4) reduces to $$\frac{D(\Delta)}{D_0} = \frac{1 + \alpha\left(\frac{L_D}{L_M}\right)^2}{1 + \left(\frac{L_D}{L_M}\right)^2}. \tag{5}$$

As $0 < \alpha < 1$ and $$\frac{L_D}{L_M}$$

is finite using a fixed $L_M$, equation (5) does not asymptote to the bulk diffusion coefficient.

In order to permit equation (4) to be effective for a wide pore size distribution and have it approach the bulk diffusion coefficient when $T_{2s}$ approaches infinity, a parameter $\Gamma$ is introduced such that $L_M$ is defined by $$L_M = \Gamma * \frac{V}{S} = \Gamma \rho T_{2s} \tag{6}$$

This definition causes $L_M$ to scale with pore size. For large pores, longer diffusion length is required to observe the transition between short-time and long-time diffusion limits. After introducing the new parameter, equation (5) will give the expected bulk diffusion coefficient in very large pores because as $T_{2s}$ approaches $\infty$, $L_M$ also approaches infinity. Substituting (6) into (4) now gives the mathematical description of the diffusion coefficient as a function of both diffusion encoding time $\Delta$ and relaxation time $T_{2s}$ with the desired asymptotic behaviors:

$$\frac{D(\Delta, T_{2s})}{D_0} = 1 - (1-\alpha)\frac{\beta\frac{L_D}{\rho T_{2s}} + (1-\alpha)\left(\frac{L_D}{\Gamma \rho T_{2s}}\right)^2}{(1-\alpha) + \beta\frac{L_D}{\rho T_{2s}} + (1-\alpha)\left(\frac{L_D}{\Gamma \rho T_{2s}}\right)^2}. \tag{7}$$

In one aspect, the generalized model in equation (7) can now be applied to samples with a wide distribution of pore sizes. Each pore size has a distinct diffusion coefficient $D(\Delta)$ and $T_{2s}$, governed by equations (2) and (3) respectively. For a fixed value of $T_{2s}$, equation (7), as a function of diffusion time $\Delta$, reduces to the conventional Padé approximation of time dependent diffusion coefficient whose fitting yields the local surface to volume ratio S/V that is relevant to the NMR measurements. For a specified diffusion time $\Delta$, equation (7) is a function of $T_{2s}$. In the special case where $T_{2s}$ approaches $\infty$, i.e. very large pores, equation (7) reduces to $$\frac{D(\Delta, T_{2s})}{D_0} = 1 - \frac{4}{9\sqrt{\pi}} \frac{1}{\rho T_{2s}} \sqrt{D_0 \Delta} \tag{8}$$

which is consistent with the known short-time limit models. See, Zielinski, L., et al., "Restricted Diffusion Effects in Staturation Estimates from 2D Diffusion-Relaxation NMR Maps," SPE Annual Technical Conference and Exhibition (2010).

Figure 2:
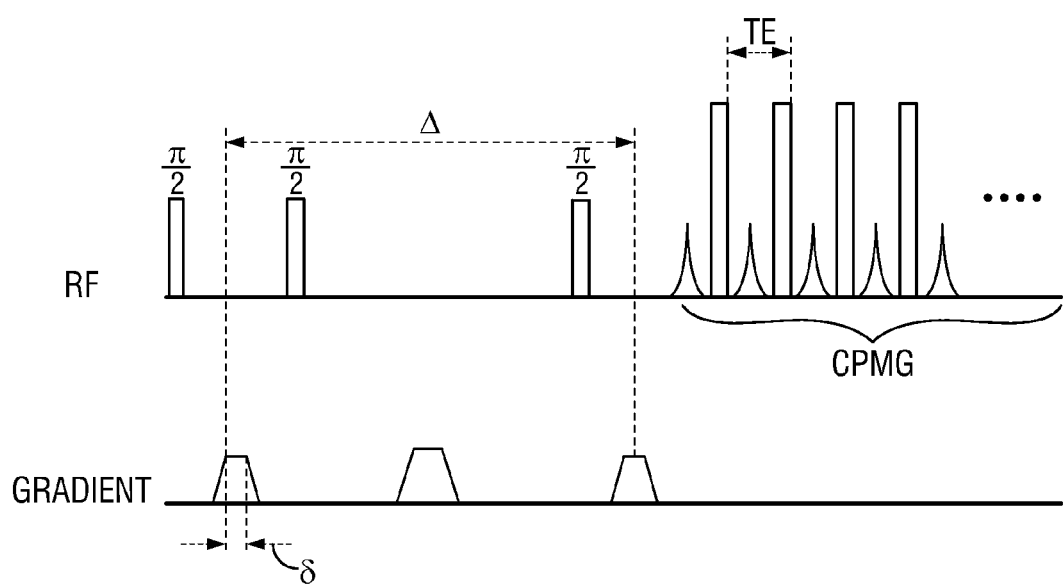
FIG. 2 is a diagram of an NMR pulse diagram sequence used for determining the surface relaxivity of a medium.
Figure 7A:
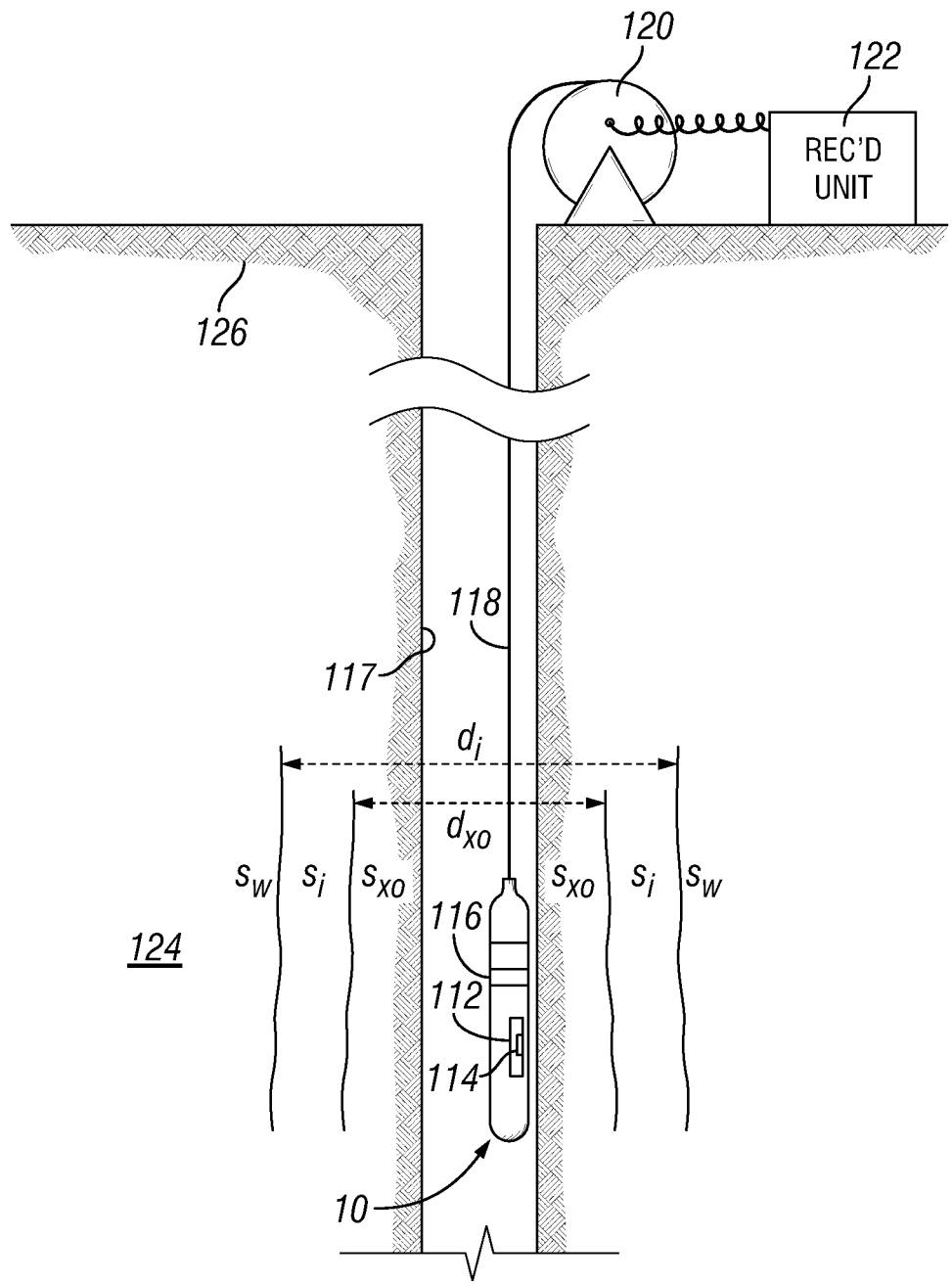
FIG. 7A shows a wireline NMR instrument deployed in a wellbore.
Figure 7B:
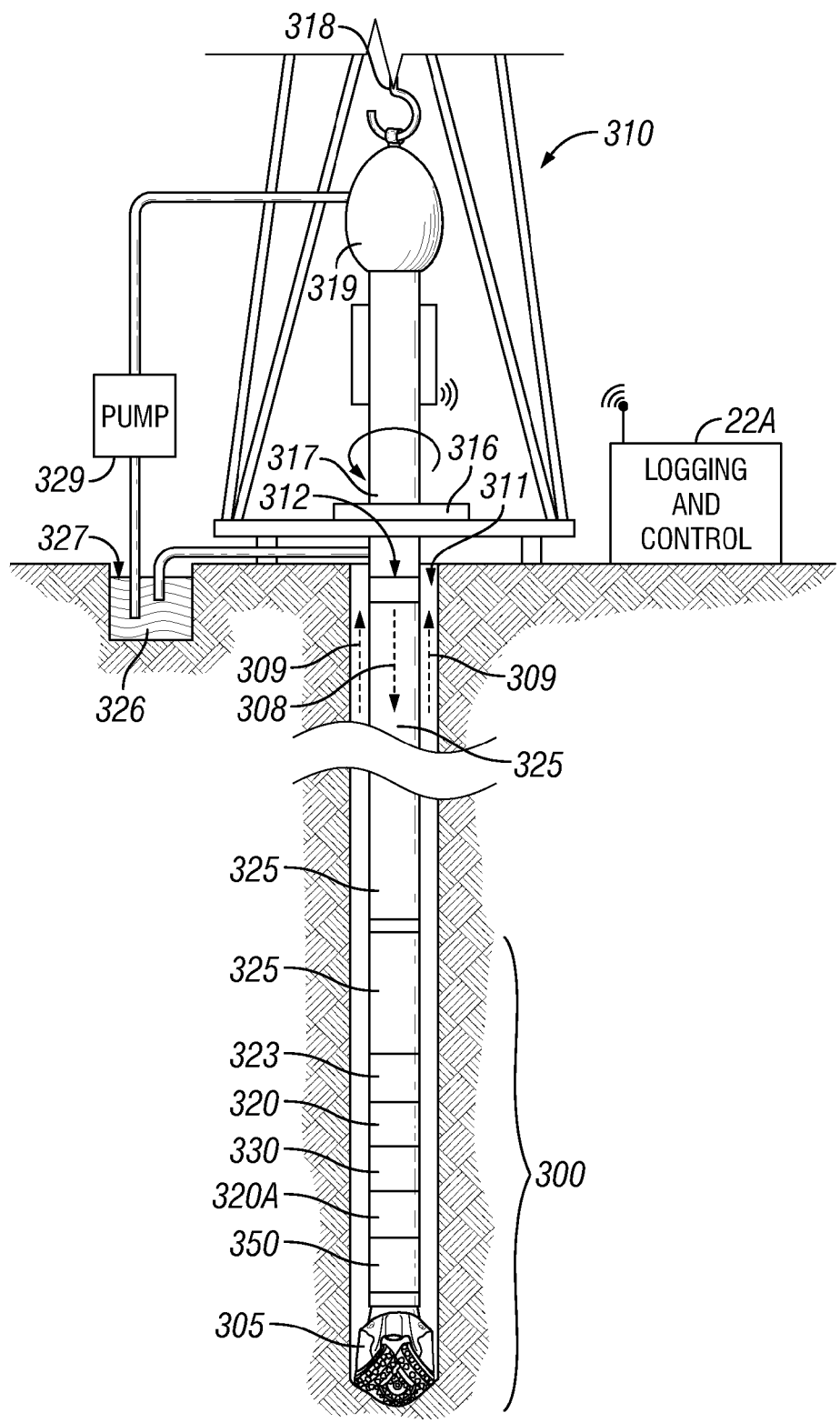
FIG. 7B shows a logging while drilling NMR instrument deployed in a wellbore.

Turning now to FIG. 1, an embodiment of a method for determining surface relaxivity of a porous medium is provided. At 10, an NMR tool such as may be used in conjunction with a core analyzer uphole or such as a downhole tool described hereinafter with respect to FIG. 7A or 7B is activated to generate a pulsed field gradient NMR pulse sequence and data (decay signals over time $\tau$) are collected. The pulse sequence is seen in FIG. 2 and may be utilized to obtain a DT$_2$ distribution containing information about the geometry of a porous medium from which surface relaxivity information may be obtained as described hereinafter. The pulse sequence of FIG. 2 includes on a first channel, two spaced RF pulses of ninety degrees followed by a CPMG sequence of a ninety degree pulse followed by a series of one hundred eighty degree pulses, with signal acquisition prior to and between the one hundred eighty degree pulses, and on a second channel, a gradient pulse between the two spaced RF pulses of ninety degree pulses, a crusher pulse between the second RF pulse and the ninety degree pulse of the CPMG sequence, and another gradient pulse between the ninety degree pulse and the first echo of the CPMG sequence. The separation of the two gradient pulses is the diffusion encoding time $\Delta$. As will be discussed hereinafter, according to one aspect, the pulse sequence of FIG. 2 is repeated for multiple different diffusion times, and for each diffusion encoding time, the pulse sequence is repeated for multiple different encoding strengths (q). In one embodiment, the encoding strengths increase in amplitude from pulse sequence to pulse sequence. In one embodiment, a first pulse sequence ($q_0$) has gradient pulses having a strength of zero; i.e., they are not present. It will be appreciated that any of many techniques may be used to encode for D(Δ) each with its own advantages and disadvantages with respect to performance and sensitivity to artifacts. See, e.g., Price, W. S., "Pulsed-field gradient nuclear magnetic resonance as a tool for studying translation diffusion: Part 1. Basic theory," Concepts in Magnetic Resonance, 9(5), pp. 299-336 (1997). Furthermore the pulse sequence components encoding for diffusion and T2 need not be in separate sections in time but may be combined together to simultaneously encode for both. For example, the ordinary CPMG sequence can be made to correlate diffusion and relaxation (T2) in a permanent gradient by, instead of varying a gradient strength, varying the echo time (te) of the entire CPMG. In this way the signal decay rate incorporate both diffusion and T2 information and varying te changes the sensitivity to diffusion and the effective diffusion encoding time (Δ) is the echo time (te). Accordingly, it should be understood that diffusion editing in the context of the present application may encompass (a) diffusion encoding that is a separate sequence from the T2 encoding sequence and (b) diffusion encoding that is at least partially integrated into the T2 encoding sequence.

Returning to FIG. 1, at 20, a $DT_2$ distribution is determined from the NMR tool signals M(q, τ) resulting from the pulse sequences of different gradient strengths. More particularly, under Gaussian approximation the measured signal by pulsed gradient stimulated echo (PGSTE) followed by CPMG detection is described by $$M(q, \tau) = \int \int f(T_2, D) e^{-\gamma^2 g^2 \delta^2 D \Delta} e^{-\frac{\tau}{T_2}} dD dT_2 \quad (9)$$

where $f(T_2,D)$ is the $DT_2$ distribution, γ is proton gyromagnetic ratio, g is pulsed gradient strength, δ is gradient duration, D is the apparent diffusion coefficient (which includes the effect of restricted diffusion), Δ is diffusion encoding time (of the gradient pulse sequence) and τ is the time in CPMG decay. The encoding strength is characterized by q=γgδ. As previously mentioned, for a given diffusion encoding time, the encoding strength is varied for a series of pulse sequences. This is accomplished by changing the pulsed gradient strength g, and/or by changing the gradient duration δ while keeping Δ fixed. Thus, M(q,τ) are the measured values for discrete values of q and τ and the collected data may be expressed as $M(q_i, \tau_j)$.

In some implementations, a 2D fast Laplace inversion algorithm is used to obtain the $DT_2$ distribution $f(T_2, D)$ (for a particular diffusion encoding time Δ) from the measured values M(q,τ). See, e.g., Venkataraman, L., et al., "Solving Fredhom integrals of the first kind with tensor product structure in 2 and 2.5 dimensions," Signal Processing, IEEE Transactions Vol. 50 pp. 1017-1026 (2002); and Song, Y.-Q., et al., "T1-T2 Correlation Spectra Obtained Using a Fast Two-Dimensional Laplace Inversion," Journal of Magnetic Resonance, Vol. 154 pp. 261-268 (2002). More particularly, equation (9) may be rewritten as $$M(q_i, \tau_j) = \Sigma_{k,l} f(T_{2,k}, D_l) e^{-q_i^2 D_l \Delta} e^{-\frac{\tau_j}{T_{2,k}}} \quad (9a)$$

which represents a linear system of equations that can be solved using a fast numerical Laplace inversion (FLI). The result is a distribution or map of signals as a function indexed by their value of $T_2$ and D; $f_{T_{2,k},D_l}$.

From the $DT_2$ distribution (also called a "$DT_2$ map"), according to some implementations, a mean or average diffusion coefficient for a particular Δ is calculated by $$\overline{D}(\Delta, T_{2s}) = \frac{\Sigma_i f(T_{2s}, D_i) * D_i^2}{\Sigma_i f(T_{2s}, D_i) * D_i} \quad (10)$$

which results in a diffusion coefficient as function of both $T_{2s}$ and diffusion encoding time Δ. More particularly, and as seen in FIG. 1 at 30, $T_2$ indices are converted into $T_{2s}$ indices for the $DT_2$ distribution data matrix $f_{T_{2,k},D_l}$ by relabeling the $T_2$ index (data axis) as a $T_{2s}$ index (data axis) utilizing $$\frac{1}{T_{2s}} = \frac{1}{T_2} - \frac{1}{T_{2b}}.$$

Then, at 35, the average diffusion coefficient $\overline{D}$ is found as a function of $T_2$ according to equation (10). Because magnetization signal decay is usually slowed down at large wave vectors due to the non-Gaussian behavior of restricted diffusion which potentially yields a secondary slow diffusion artifact peak, the $\overline{D}(\Delta, T_{2s})$ calculation of equation (10) weights more strongly the large diffusion coefficients. As a result, the effect of non-Gaussian behavior is minimized to give a more accurate determination of the apparent diffusion coefficient. In another embodiment, instead of utilizing equation (10), the average diffusion coefficient is calculated according to $$\overline{D}(\Delta, T_{2s}) = \sqrt{\frac{\Sigma_i f(T_{2s}, D_i) * D_i^2}{\Sigma_i f(T_{2s}, D_i)}}. \quad (10a)$$

In some implementations, instead of utilizing equation (10) or equation (10a), the average diffusion coefficient is calculated according to $$\overline{D}(\Delta, T_{2s}) = \frac{\Sigma_i f(T_{2s}, D_i) * D_i}{\Sigma_i f(T_{2s}, D_i)}. \quad (10b)$$

At 40, the $T_2$ distribution across diffusion coefficients $D_i$ for a particular diffusion time Δ is calculated according to $$g(\Delta, T_{2s}) = \Sigma_D f_\Delta(T_{2s}, D_i) \quad (11)$$

Then, at 50, a determination is made as to whether data for all diffusion times Δ have been obtained and/or processed. If not, the method is repeated for a new diffusion time by generating a pulsed field gradient NMR pulse sequence with the new diffusion time and collecting data at 10, determining the $DT_2$ distribution at 20, finding the average diffusion coefficient $\overline{D}$ at 35 (after relabeling at 30), and calculating the $T_2$ distribution across diffusion coefficients $D_i$ at 40. It is noted that instead of sequentially generating the pulse sequence and collecting data followed by determining the $DT_2$ distribution, finding the average diffusion coefficient, etc., some or all pulse sequences may be generated and data collected prior to determining the $DT_2$ distribution, finding the average diffusion coefficient, etc.

With the $T_2$ distributions and the average diffusion coefficients $\overline{D}$ calculated for all $\Delta$, it is then possible to make a determination of the surface relaxivity $\rho$. More particularly, at 60, a minimization procedure is utilized where equation (7) is fitted to the 2D data set $\overline{D}(\Delta,T_{2s})$ in order to extract a determination of the surface relaxivity $\rho$ along with other (unknown) parameters such as the bulk diffusion coefficient $D_0$, the asymptotic value $\alpha = D(\infty)/D_0$, and parameter $\Gamma = L_m/\rho T_{2s}$. In the minimization procedure, the cost function is constructed as follows:

$$\text{err} = \Sigma_{\Delta,T_{2s}} \{g(\Delta,T_{2s}) * [\log D_{fit}(\Delta,T_{2s}) - \log \overline{D}(\Delta,T_{2s})]\}^2 \quad (12)$$

where $D_{fit}(\Delta,T_{2s})$ is the fitted function of equation (7) whose unknown parameters are chosen to cause the fitted function to most nearly approximate the data set of average diffusion coefficients, thereby causing equation (12) to be a minimum, and $g(\Delta,T_{2s})$ is the error weighing function, i.e. the $T_2$ distribution calculated according to equation (11). In the minimization of equation (12), a logarithmic error is used so that it equally weighs the faster and slower diffusion coefficients (due to different pore sizes). In other embodiments, equation (12) is modified to include a non-logarithmic error. In those other embodiments, the slower diffusion coefficient region will have little effect on the fitting.

Alternatively or additionally, in order to generate a function relating Diffusion and T2, from a DT2 map, one can also calculate various weighted means $T_{2s}$ as a function of diffusion (e.g., $\overline{T_{2s}}(D_\Delta)$) to compute the functional relation between D and $T_2$. For example, the log mean $T_2$ as a function of D:

$$\overline{T_{2s}}(D_\Delta) = 10^{\frac{\Sigma_i F(T_{2s,i}, D_\Delta) \log_{10} T_{2s,i}}{\Sigma_i F(T_{2s,i}, D_\Delta)}}$$

or the linear mean $$\overline{T_{2s}}(D_\Delta) = \frac{\Sigma_i F(T_{2s,i}, D_\Delta) T_{2s,i}}{\Sigma_i F(T_{2s,i}, D_\Delta)}$$

In some implementations, the pulsing at 10, the determining of the $DT_2$ distribution at 20, the relabeling at 30, the finding of the average diffusion coefficient $\overline{D}$ as a function of $T_2$ according to equation (10) at 35, and the calculation of a $T_2$ distribution at 40 are done for a single encoding time $\Delta$, and equation (7) is fitted to $\overline{D}(T_{2s})$ in order to extract a determination of the surface relaxivity $\rho$ along with other (unknown) parameters such as the bulk diffusion coefficient $D_0$, the asymptotic value $\alpha = D(\infty)/D_0$, and parameter $\Gamma = L_m/\rho T_{2s}$.

According to one aspect, it will be appreciated that the method of FIG. 1 is accomplished utilizing information obtained from NMR data only, and does not require other non-NMR measurements such as measurements of formation parameters such as porosity.

According to one embodiment, multiple determinations of surface relaxivity may be made along a distance or depth in a borehole and the determinations may be displayed as a log according to distance or depth in a borehole. According to another embodiment, the determination of surface relaxivity may be displayed on paper or on a screen.

In order to confirm the method of FIG. 1, four packed glass beads (class IV soda lime spheres) were used as a model system. The glass beads had nominal diameters of 50 μm, 100 μm, 200 μm and 500 μm respectively. The diameter variation was about ±15% and spherical percentage was greater than 85%. The as-received glass beads were cleaned with 1M HCl at room temperature for one hour and then thoroughly washed with deionized water to remove paramagnetic impurities and surface contaminations. The cleaned glass beads were saturated with deionized water whose bulk relaxation time $T_{2b}$ was 2.3 s. The beads' pack information with respect to bead sizes, porosities and $T_2$ relaxation times are summarized in Table 1 below.

In accordance with FIG. 1, NMR measurements were carried out on a Magritek Rock Core Analyzer ($^1$H frequency 2 MHz) at room temperature. The gradient was calibrated using bulk deionized water in 3 mm capillaries to avoid convection. Pulsed gradient stimulated echo (PGSTE) was used for diffusion encoding and the standard CPMG was used for data acquisition as depicted in FIG. 2. The echo time TE between two π pulses was 167 μs. Signal decay due to diffusion in background gradient (<0.02 G/cm) during the CPMG acquisition was negligible.

Figure 3A:
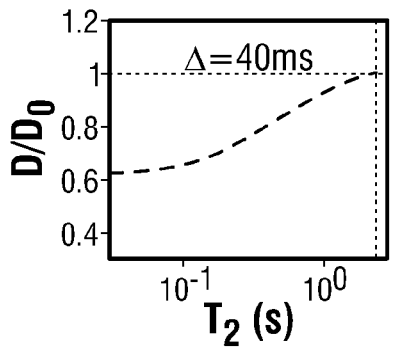
FIGS. 3a-3e are $DT_2$ distribution plots and fitting results for five different diffusion encoding times for a medium with elements having a first diameter size.
Figure 3B:
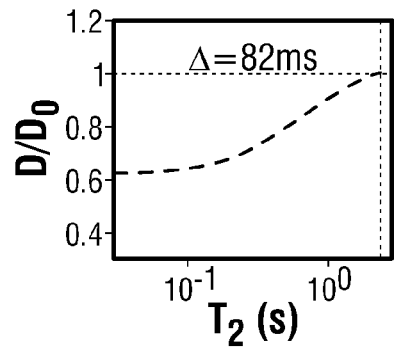
Figure 3C:
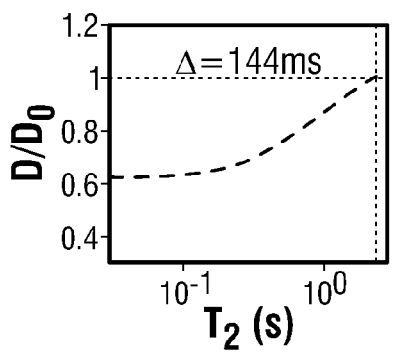
Figure 3D:
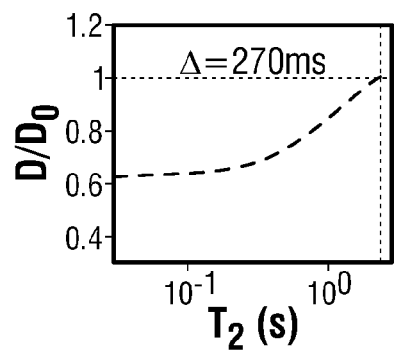
Figure 3E:
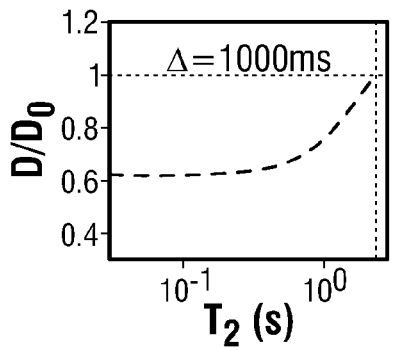
Figure 3F:
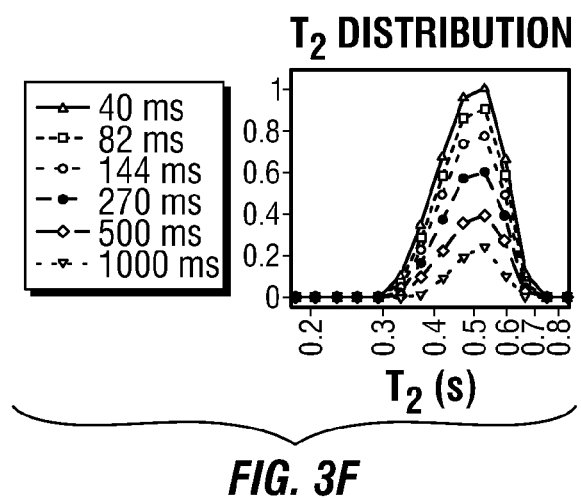
FIG. 3f is a $T_2$ distribution for the medium having a first diameter size.
Figure 4A:
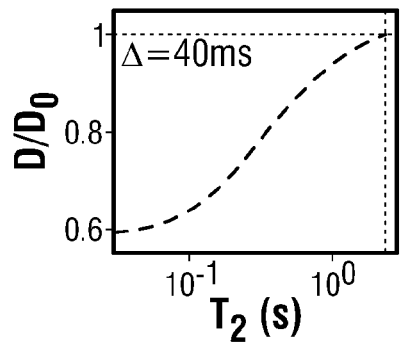
FIGS. 4a-4e are $DT_2$ distribution plots and fitting results for five different diffusion encoding times for a medium with elements having a second diameter size.
Figure 4B:
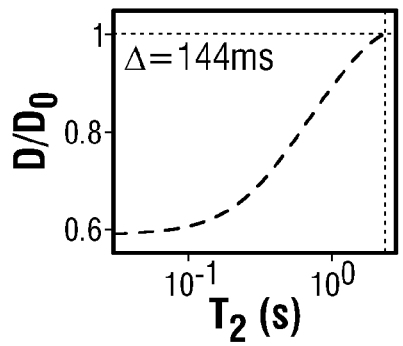
Figure 4C:
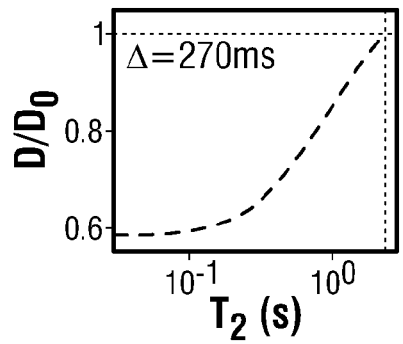
Figure 4D:
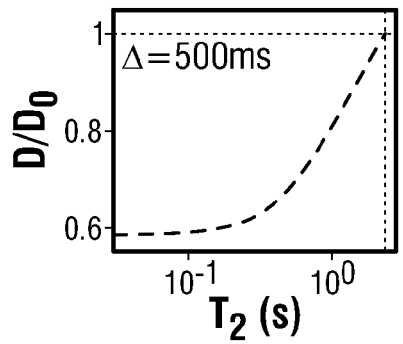
Figure 4E:
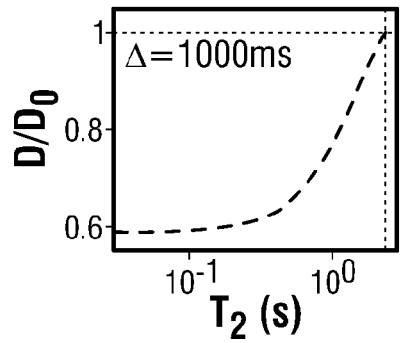
Figure 4F:
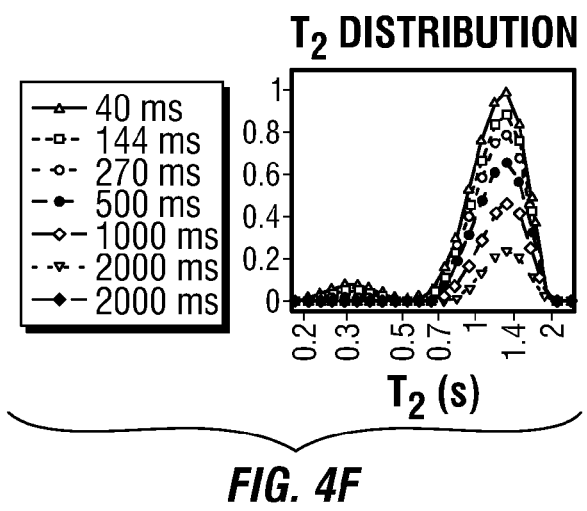
FIG. 4f is a $T_2$ distribution for the medium having a second diameter size.

The measured signal resulting from the NMR pulse sequences was processed according to FIG. 1. Representative fitting results on glass beads are shown in subplot FIGS. 3a-3e (100 μm beads) and FIGS. 4a-4e (500 μm beads). The $\overline{D}(\Delta,T_{2s})$ data are displayed in gray scale according to the weighing function $g(\Delta,T_{2s})$, i.e. $T_2$ distribution. On each subplot, $g(\Delta,T_{2s})$ has been normalized for display purposes. Restricted diffusion is clearly seen as diffusion time increases from 40 ms (FIGS. 3a and 4a) to 1 s (FIGS. 3e and 4e), but the $T_2$ distribution as seen in FIGS. 3f and 4f remains similar for all $DT_2$ maps except the intensity decreases. Equation (7) is able to fit the diffusion coefficient behavior depending on $T_2$ relaxation time and diffusion coefficient very well.

The multiple $DT_2$ global fitting parameters are summarized in Table 1. Bulk liquid diffusion coefficient $D_0$ varies a little bit because temperature is not strictly controlled and the water diffusion coefficient depends sensitively on temperature. The resultant long time limit diffusion coefficient $D(\infty)/D_0\alpha$ falls between 0.59 to 0.66, close to the expected value $\alpha = \sqrt{\phi} = 0.62$ for packed glass beads with porosity $\phi$ of about 0.37. It is interesting to note that the parameter $\Gamma$ stays fairly constant although the bead diameter changed from 50 μm to 500 μm. This result is in agreement with the above suggestion that $L_M$ scales with pore size (and bead size).

TABLE 1

Sample information and multiple $DT_2$ global fitting results based on eq. (7).

| Sample name | size range (μm) | porosity φ | $T_2$ (s) | ρ (μm/s) | $D_0$ ($10^{-9}$ m/s²) | α | Γ |
|---|---|---|---|---|---|---|---|
| 50 μm bead | 45-63 | 37% | 0.27 | 14.9 | 2.19 | 0.66 | 2.5 |
| 100 μm bead | 90-125 | 36% | 0.48 | 16.5 | 2.18 | 0.62 | 2.1 |
| 200 μm bead | 180-250 | 37% | 0.66 | 21.8 | 2.15 | 0.62 | 2.1 |
| 500 μm bead | 425-600 | 38% | 1.19 | 20.7 | 2.22 | 0.59 | 1.9 |
| Berea | Null | 23% | distribution | 19.4 | 2.15 | 0.56 | 2.1 |
| Fontainebleau | Null | 5.6% | distribution | 3.0 | 2.15 | 0.62 | 1.9 |

To further estimate the reliability of the method, the fitted surface relaxivity ρ was compared to the value calculated by $$\rho = \frac{d * \phi}{6 * T_{2s} * (1-\phi)} \quad (13)$$

where φ is porosity and d is nominal bead size. Here $$\frac{6*(1-\phi)}{d*\phi}$$

can be used as a good estimate of surface volume ratio S/V because the bead size is fairly uniform and bead shape is mostly spherical. Since the diffusion length is in the order of micrometers, the surface roughness in nanometer scale should not affect the NMR relevant S/V. The calculated surface relaxivity using the method of FIG. 1 are shown in Table 2 along with single $DT_2$ fitting results using fixed $L_M$=100 μm and $L_M$=20 μm respectively.

TABLE 2

Comparison between multiple $DT_2$ global fit and fixed $L_M$ single $DT_2$ fit

| Nominal bead size d | Calculated ρ (μm/s) by Eq. 13 | Multiple $DT_2$ ρ (μm/s) | Single $DT_2$ $L_M$ = 100 μm, Δ = 82 ms, ρ (μm/s) | Single $DT_2$ $L_M$ = 20 μm, Δ = 82 ms, ρ (μm/s) |
|---|---|---|---|---|
| 50 μm | 16.0 | 14.9 | 10.1 | 12.2 |
| 100 μm | 15.5 | 16.5 | 9.8 | 13.9 |
| 200 μm | 21.2 | 21.8 | 12.6 | 28.2 |
| 500 μm | 20.7 | 20.7 | 17.1 | Null |

It is interesting to note that multiple $DT_2$ fitted surface relaxivity is consistent with the calculated value for all four beads within a ±7% error. However, fixed $L_M$ parameterization on a single $DT_2$ fitting, while providing a fairly good estimate for a specific bead size, is seen to not satisfy all pore sizes with multiple length scales. For example, while the fitting on 500 μm beads using $L_M$=100 μm yields ρ=17.1 μm/s, which is only 17% smaller than the calculated 20.7 μm/s using equation (13), on 100 μm beads, it yields ρ=9.8 μm/s which is 37% smaller than the expected surface relaxivity 15.5 μm/s. The misfit is even more serious for a smaller fixed $L_M$, for instance, $L_M$=20 μm. For $L_M$=20 μm, the 500 μm beads could not be fitted with this parameterization because the asymptotic value in equation (5) is significantly below 1.

Figure 5A:
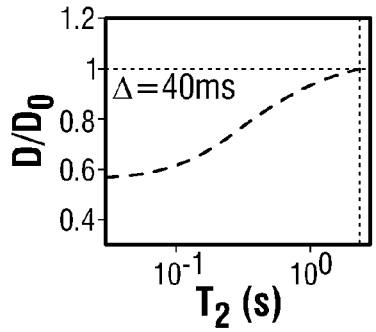
FIGS. 5a-5e are $DT_2$ distribution plots and fitting results for five different diffusion encoding times for a Berea sandstone rock core sample.
Figure 5B:
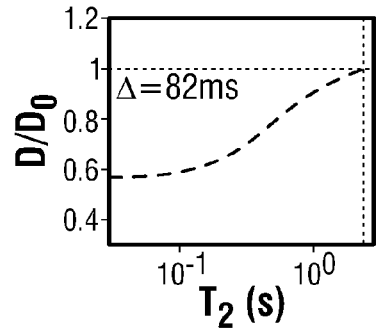
Figure 5C:
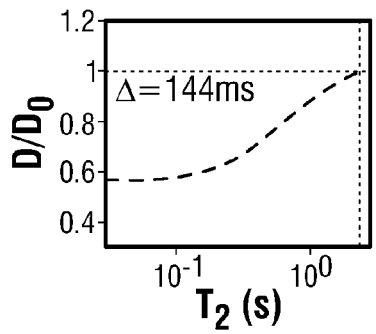
Figure 5D:
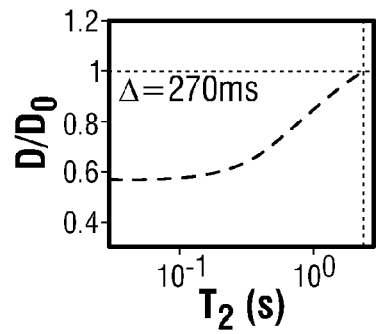
Figure 5E:
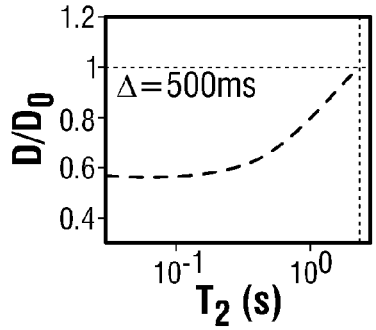
Figure 5F:
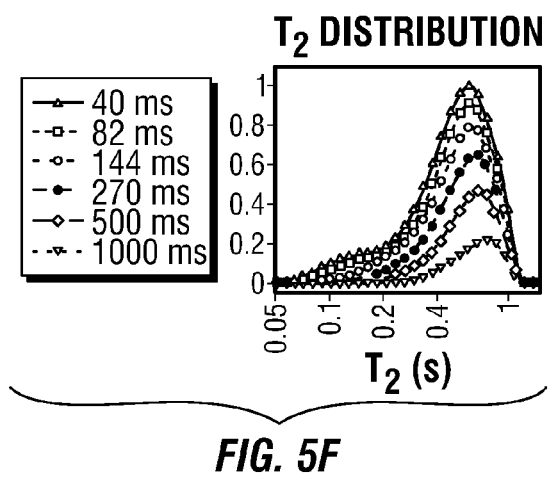
FIG. 5f is a $T_2$ distribution for the Berea sandstone rock core sample.

NMR $DT_2$ experiments were also carried out on Berea sandstone sample (porosity 23.17%, permeability 1026 mD) and Fontainebleau sandstone sample (porosity 5.63%, permeability 5.15 mD) rock cores where the multiple $DT_2$ global fitting method of FIG. 1 was applied to determine the surface relaxivities of the samples. FIGS. 5a-5e show the results on the Berea sandstone rock core sample with a wide $T_2$ distribution indicated in the subplot of FIG. 5f. As diffusion time increases, the smaller $T_2$ components gradually disappear, shifting the $T_2$ distribution peak towards larger $T_2$ values. The fitting of the method yields a surface relaxivity 19.3 μm/s, which is almost twice that of a previously reported value (9.8 μm/s) on a Berea sample with porosity 22% and permeability 380 mD. However, the previously reported value was based on a $T_2$ distribution peak of 1.0 s while the measured $T_2$ peak of this experiment was at 0.60 s. Thus, the difference in surface relaxivity might be caused by lithology or pore size differences. In FIGS. 5a-5e, it can be seen that the global fitting based on equation (7) works very well for smaller diffusion time, but an apparent deviation is observed for Δ=500 ms where the $\bar{D}(\Delta, T_{2s})$ data lie below the fitted curve for the small and large $T_2$ region. The $\bar{D}(\Delta, T_{2s})$ data has a saddle-like shape, probably due to an internal gradient and the resolution limit of the fast Laplace inversion algorithm on a weak signal. However, this is accounted for by the weighing of the $T_2$ distribution which focuses more on the well-behaved region. With the method of FIG. 1, the effect of an abnormally small $T_2$ and a large $T_2$ region is minimal because the corresponding signal is very weak.

Figure 6A:
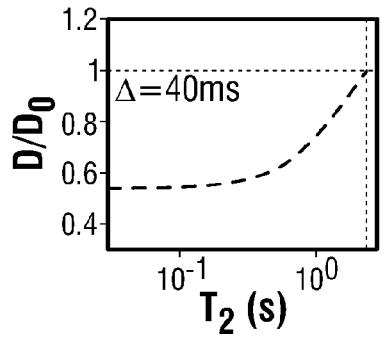
FIGS. 6a-6e are $DT_2$ distribution plots and fitting results for five different diffusion encoding times for a Fontaineblue sandstone rock core sample.
Figure 6B:
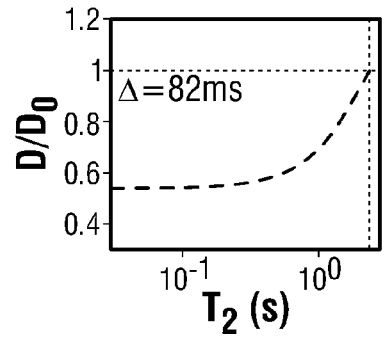
Figure 6C:
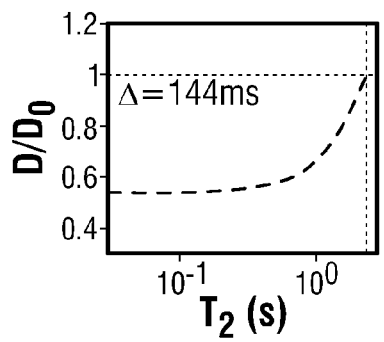
Figure 6D:
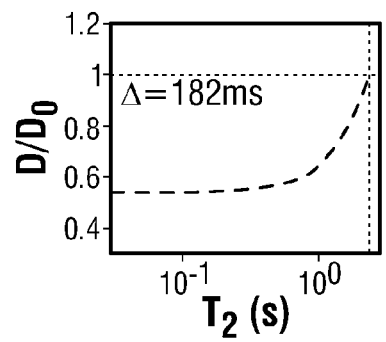
Figure 6E:
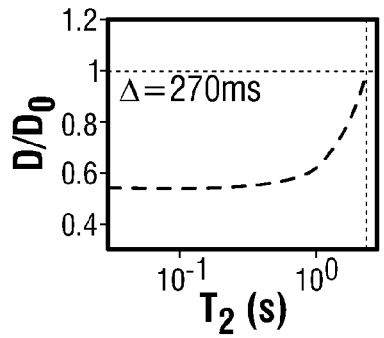
Figure 6F:
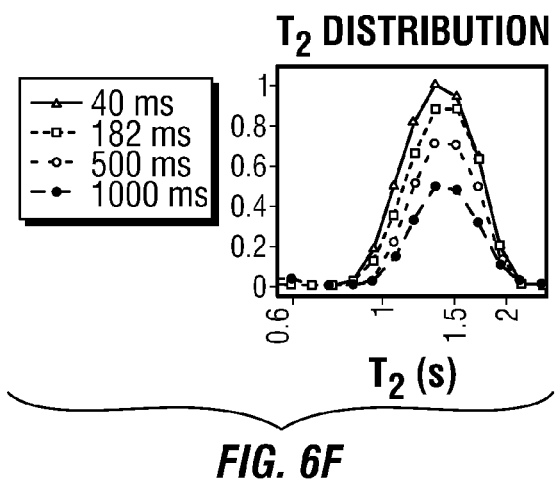
FIG. 6f is a $T_2$ distribution for the Fountainblue sandstone rock core sample.

Fontainebleau sandstone results are shown in FIGS. 6a-6e. The $T_2$ distribution shown in FIG. 6e is between 1 s and 2 s, indicating a relative narrow pore size distribution. However some abnormal features are present on the $\bar{D}(\Delta, T_{2s})$ data. For example, on the Δ=40 ms data, the diffusion coefficient decreases with $T_2$ relaxation time. This could be caused by the resolution of the 2D inversion considering the narrow $T_2$ distribution and the weak signal due to low porosity. The error due to 2D inversion can be averaged out to give a reasonable fitting result. The fitted surface relaxivity is 3.0 μm/s and other parameters fall into the expected range (Table 1). The small surface relaxivity is in line with the lithology and confirmed by the qualitative observation that its $T_2$ peak is at 1.36 s, much larger than that of Berea sandstone (0.60 s), even though its pore sizes are smaller than that of Berea. Prior work reported surface relaxivities in the range 5-10 μm/s on a suite of 7 Fontainebleau sandstone samples. Particularly, on a Fontainebleau sample (porosity 6.4%, permeability 5.4 mD) similar to the investigated one, a surface relaxivity 5.1 μm/s was obtained. While the relaxivity determination obtained using the method of FIG. 1 of 3.0 μm/s is smaller than reported value of 5.1 μm/s, the results are consistent with the fact that the reported $T_2$ distribution peak was at 0.83 s while the $T_2$ distribution peak in the experiment was at 1.36 s.

It should be appreciated that the method of FIG. 1 may be carried out by any of numerous apparatus. Thus, in one embodiment, the method may be accomplished in an (uphole) laboratory through the use of a core sampler NMR apparatus such as, by way of example only, a Magritek Rock Core Analyzer. In another embodiment, the method may be accomplished utilizing downhole equipment such as shown in FIG. 7A or 7B.

FIG. 7A shows an example nuclear magnetic resonance ("NMR") wireline well logging instrument 110 disposed in a wellbore 117 drilled through subsurface rock formations 126, 124. The instrument 110 is attached to one end of an armored electrical cable ("wireline") 118. The cable 118 may be extended into the wellbore 117 and withdrawn therefrom by a spooling device such as a winch 120 of types well known in the art. The cable 118 includes one or more insulated electrical conductors and may include one or more optical fibers to communicate signals between the instrument 110 and a recording unit 122 disposed at the Earth's surface. The recording unit 122 may include a processor or computer having an optional screen or printer type data display, input controls and a data recording device for storage of signals (e.g., NMR measurements) communicated from the well logging instrument 110, as well as for storing or displaying calculated results made from NMR measurements made by the instrument 110 as described hereinafter. The well logging instrument 110 may also include a downhole processor as described hereinafter.

The NMR instrument 110 includes a magnet 112 for inducing a static magnetic field in the formations 124, 126 having a predetermined spatial distribution of magnetic field amplitude. According to one aspect, magnet 112 may be supplemented by an electromagnet configured to impart a selected magnitude gradient field superimposed on the static homogenous field. The NMR instrument 110 may be arranged as disclosed in U.S. Patent Application Publication No. 20140184220, and/or in U.S. Pat. No. 5,796,252 which are both hereby incorporated by reference herein in their entireties. As the instrument 110 is moved along the interior of the wellbore 117, nuclei in the formations surrounding the wellbore are magnetically polarized along the direction of the magnet's 112 field. The instrument 110 also includes an antenna for inducing radio frequency ("RF") magnetic fields in the formations, and for detecting radio frequency signals induced by NMR phenomena excited in the formations by the static and RF magnetic fields. The particular portion of the formations adjacent to the wellbore from which the NMR signals originate depends on, among other factors, the spatial amplitude distribution of the static magnetic field and the RF frequency used to induce NMR phenomena in the formations. Some magnets may induce a region of substantially homogeneous field amplitude in a particular region in the formations; other types of magnets may induce static fields having a selected amplitude gradient in a particular region of interest. However arranged, the NMR instrument 110 is equipped to generate NMR pulses such as shown in FIG. 2.

Some formations, for example the one illustrated at 124 in FIG. 7A may be permeable and/or contain movable hydrocarbon in the pore spaces thereof. Proximate the wall of the wellbore 117, a portion of the formation 124 may be subjected to sufficient infiltration of the liquid phase of a fluid ("drilling mud"), called "mud filtrate", used to drill the wellbore 117, that substantially all of the mobile connate fluids in the pore spaces of the formation 124 are displaced by the mud filtrate. Depending on, for example, the fractional volume of pore space (porosity) of the formation 124, and the filtrate characteristics of the drilling mud, the mud filtrate will fully displace all the mobile connate fluids to a depth represented by $d_{xo}$ in FIG. 7A. The foregoing is referred to as the diameter of the "flushed zone." Partial displacement of connate fluid is shown extending to a diameter represented by $d_i$, which is used to represent the diameter of the "invaded zone." At a certain lateral depth in the formation 124, beyond the diameter of the invaded zone, connate fluid is substantially undisturbed. A quantity of interest in determining possible fluid production in from the formation is the fractional volume of the pore space that is occupied by water (and its complement assumed to be occupied by hydrocarbons). In the uninvaded zone, such fractional volume, called "saturation", is represented by $S_w$. Invaded zone and flushed zone water saturations are represented, respectively, by $S_i$ and $S_{xo}$.

The example instrument shown in FIG. 7A is only for purposes of explaining a source of measurements that may be used and is not intended to limit the configurations of NMR well logging instrument that may be used to provide measurements of various embodiments hereof. Further, reference to portions of formations that contain hydrocarbon are only for purposes of illustrating general principles of NMR well logging; as certain measurements of NMR properties may be made in formations known to be fully water saturated to simplify calculations of formation properties made from the NMR measurements.

FIG. 7B illustrates a well site system in which an NMR well logging instrument can be conveyed using a drill string or other pipe string for measurement during the drilling of the wellbore, or during other pipe string operations associated with the construction of a wellbore such as circulating, washing, reaming and "tripping." The well site can be onshore or offshore. In the example system of FIG. 7B, a wellbore 311 is drilled through subsurface formations by rotary drilling in a manner that is well known in the art. Other examples of NMR instruments can be used in connection with directional drilling apparatus and methods. Accordingly, the configuration shown in FIG. 7B is only intended to illustrate a possible source of NMR measurements and is not intended to limit the scope of this disclosure.

A drill string 312 is suspended within the wellbore 311 and includes a bottom hole assembly ("BHA") 300 proximate the lower end thereof. The BHA 300 includes a drill bit 305 at its lower end. The surface portion of the well site system includes a platform and derrick assembly 310 positioned over the wellbore 311, the assembly 310 including a rotary table 316, kelly 317, hook 318 and rotary swivel 319. The drill string 312 is rotated by the rotary table 316, which is itself operated by well known mechanisms. The rotary table 316 engages the kelly 317 at the upper end of the drill string 312. The drill string 312 is suspended from the hook 318. The hook 318 is attached to a traveling block, through the kelly 317 and the rotary swivel 319 which permits rotation of the drill string 312 relative to the hook 318. As is well known, a top drive system could alternatively be used instead of the kelly 317 and rotary table 316 to rotate the drill string 312 from the surface. The drill string 312 may be assembled from a plurality of segments 325 of pipe and/or collars threadedly joined end to end.

In the present example, the surface system further includes drilling fluid ("mud") 326 stored in a tank or pit 327 formed at the well site. A pump 329 delivers the drilling fluid 326 to the interior of the drill string 312 via a port in the swivel 319, causing the drilling fluid 326 to flow downwardly through the drill string 312 as indicated by the directional arrow 308. The drilling fluid 326 exits the drill string 312 via water courses, or nozzles ("jets") in the drill bit 305, and then circulates upwardly through the annulus region between the outside of the drill string and the wall of the borehole, as indicated by the directional arrows 309. In this manner, the drilling fluid 326 lubricates the drill bit 305 and carries formation cuttings up to the surface, whereupon the drilling fluid 326 is cleaned and returned to the pit 327 for recirculation.

The bottom hole assembly 300 of the illustrated example may include a logging-while-drilling LWD) module 320, a measuring-while-drilling (MWD) module 330, a steerable directional drilling system such as a rotary steerable system and/or an hydraulically operated motor such as a steerable motor, and the drill bit 305.

The LWD module 320 is housed in a special type of drill collar, such as, for example, one known in the art, and may contain one or a plurality of known types of well logging instruments. It will also be understood that more than one LWD and/or MWD module may be used, e.g. as represented at 320A. (References, throughout, to a module at the position of LWD module 320 can alternatively mean a module at the position of MWD module 320A as well.) The LWD module 320A typically includes capabilities for measuring, processing, and storing information, as well as for communicating with the surface equipment. In the present embodiment, the LWD module 320 includes an NMR measuring instrument. An example configuration of such instrument is explained above with reference to FIG. 7A.

The MWD module 330 is also housed in a special type of drill collar, such as, for example, one known in the art, and can contain one or more devices for measuring characteristics of the drill string and drill bit. The MWD module 330 further includes an apparatus for generating electrical power for the downhole portion of the well site system. Such apparatus typically includes a turbine generator powered by the flow of the drilling fluid 326, it being understood that other power and/or battery systems may be used while remaining within the scope of the present invention. In the present example, the MWD 330 module may include, for example, one or more of the following types of measuring devices: a weight-on-bit measuring device, a torque measuring device, a vibration measuring device, a shock measuring device, a stick slip measuring device, a direction measuring device, and an inclination measuring device.

The foregoing examples of wireline and drill string conveyance of a well logging instrument are not to be construed as a limitation on the types of conveyance that may be used for the well logging instrument. Any other conveyance known in the art may be used, including without limitation, slickline (solid wire cable), coiled tubing, well tractor, and production tubing.

A recording unit 122A may be disposed at the surface and may include data acquisition, recording, input, control and display devices similar to those of the recording unit shown at 122 in FIG. 7A.

In example methods, measurements of nuclear magnetic resonance ("NMR") properties of subsurface formations may be made at one or more lateral depths into the formations adjacent to the wellbore. A NMR instrument, as explained above with reference to FIGS. 7A and 7B, can be moved along a wellbore drilled through subsurface formations.

In some examples, NMR measurements may be made using an instrument identified by the trademark MR Scanner which is a trademark of the assignee the present invention. In other examples, the NMR measurements may be made using an instrument identified by the trademark CMR-Plus which is also a trademark of the assignee of the present invention. The NMR instrument, irrespective of type, is generally moved longitudinally along the wellbore and a record with respect to depth in the wellbore is made of the NMR properties of the various formations. The foregoing identified MR Scanner instrument, in particular, can make measurements of NMR properties of the formations at a plurality of different, defined lateral depths of investigation. The lateral depths of investigation for the foregoing instrument are about 1.5 inches (3.8 cm), 2.7 inches (6.9 cm) and 4 inches (10.2 cm) from the wall of the wellbore. As explained above, the lateral depth of investigation of any particular NMR measurement is defined by the spatial distribution of the amplitude of the static magnetic field and the frequency of the RF magnetic field used to excite NMR phenomena. The example instruments described herein are not limitations but are provided as illustrative examples.

According to some examples, the processor or computer recording system 122 that is provided may include one or more processors located uphole and/or downhole and can be used to implement or perform any of the methods and processes for analyzing described hereinafter. Where, for example, the method is to be accomplished in a laboratory through the use of a core sampler NMR apparatus, it will be appreciated that any processor or computer recording system may be located uphole. The terms "processor" and "computer recording system" (hereinafter "processing system") should not be construed to limit the embodiments disclosed herein to any particular device type or system. The processing system may be, for example, one or more laptop computer, one or more desktop computer, and/or one or more mainframe computer. The processing system may also include a processor (e.g., a microprocessor, microcontroller, digital signal processor, or general purpose computer) for executing any of the methods and processes hereinafter described. In this regard, the term "processor" as used herein should be understood, unless indicated to the contrary, to encompass single or multiple processing units disposed in any suitable location or locations. The processing system may further include a memory such as a semiconductor memory device (e.g., a RAM, ROM, PROM, EEPROM, and/or Flash-Programmable RAM), a magnetic memory device (e.g., a diskette and/or fixed disk), an optical memory device (e.g., a CD-ROM), a PC card (e.g., PCMCIA card), or other memory device. This memory may be used to store, for example, fundamental equation and/or instructions for performing the processes described above.

Any of the methods and processes hereinafter described can be implemented as computer program logic for use with the processing system. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the processing system. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

As used herein (including in the claims), a recitation in the general form of "at least one of [A] and [B]" should be construed as disjunctive. That is, this recitation should be construed to include each of the following: (i) both [A] and [B] are present; (ii) [A] is present, but [B] is not, and (iii) [B] is present, but [A] is not.

There have been described and illustrated herein several embodiments of methods of determining surface relaxivity of a porous medium. While particular embodiments and aspects have been described, it is not intended that the disclosure be limited thereto, and it is intended that the claims be as broad in scope as the art will allow and that the specification be read likewise. Thus, while certain equations for obtaining an average diffusion coefficient were described, other equations could be utilized. Similarly, while a particular minimization equation was described, other minimization equations or techniques could be utilized. It will therefore be appreciated by those skilled in the art that yet other modifications could be made. Accordingly, all such modifications are intended to be included within the scope of this disclosure as defined in the following claims. In the claims, means-plus-function clauses, if any, are intended to cover the structures described herein as performing the recited function and not only structural equivalents, but also equivalent structures. It is the express intention of the applicant not to invoke 35 U.S.C. §112, paragraph 6 for any limitations of any of the claims herein, except for those in which the claim expressly uses the words 'means for' together with an associated function. Moreover, it should be understood that any of the features described herein may be provided in any suitable combination.

What is claimed is:

1. A method of determining surface relaxivity of a porous medium, comprising:
    applying multiple nuclear magnetic resonance (NMR) diffusion editing Carr-Purcell-Meiboom-Gill (CPMG) pulse sequences to the porous medium, wherein the diffusion editing CPMG pulse sequences have gradient pulses for diffusion editing separated by a diffusion encoding time $\Delta$;
    receiving NMR data generated by the pulse sequences;
    processing the received NMR data to obtain a distribution $f(T_2,D)$ for the diffusion encoding time $\Delta$, where $T_2$ is transverse relaxation time and D is diffusion coefficient;
    repeating the applying, the receiving, and the processing at least one time for pulse sequences having different respective diffusion encoding times $\Delta$ to obtain respective distributions $f(T_2,D)$ corresponding respectively to the different diffusion encoding times $\Delta$; and
    utilizing the respectively obtained distributions $f(T_2,D)$ together to generate a surface relaxivity ($\rho$) determination.

2. The method according to claim 1, further comprising:
    calculating a mean diffusion coefficient $\overline{D}(T_{2s})$ for each $T_2$ value of each distribution $f(T_2,D)$, where $T_{2s}$ is the transverse relaxation time due to surface relaxation; and
    calculating a respective $T_2$ distribution $g(T_{2s})$ for each distribution $f(T_2,D)$,
    wherein the surface relaxivity ($\rho$) determination is generated utilizing the calculated $T_2$ distributions and the calculated mean diffusion coefficients ($T_{2s}$).

3. The method according to claim 1, further comprising:
    calculating a weighted mean transverse relaxation time $\overline{T_{2s}}(D)$ for each D value of each distribution $f(T_2,D)$ to compute a functional relation between D and $T_2$,
    wherein the surface relaxivity ($\rho$) determination is generated utilizing the functional relation between D and $T_2$.

4. The method according to claim 1, wherein the generating multiple nuclear magnetic resonance CPMG pulse sequences comprises determining the diffusion encoding time $\Delta$ such that the characteristic diffusion length of a saturated fluid expected to be disposed in the porous medium corresponds to an expected pore size of the porous medium.

5. The method according to claim 1, wherein:
    the utilizing comprises conducting a data-fitting error minimization.

6. The method according to claim 5, wherein:
    the data-fitting error minimization comprises choosing values for the surface relaxivity and at least one parameter to cause a fitting function of the surface relaxivity and the at least one parameter to closely approximate a data set of the average diffusion coefficients $\overline{D}(\Delta,T_{2s})$.

7. The method according to claim 6, wherein:
    the data-fitting error minimization comprises utilizing a logarithmic error.

8. The method according to claim 7, wherein:
    the logarithmic error is defined according to err=$\Sigma_{\Delta T_{2s}}\{g(\Delta,T_{2s})*[\log D_{fit}(\Delta,T_{2s})-\log \overline{D}(\Delta,T_{2s})]\}^2$, where $D_{fit}(\Delta,T_{2s})$ is the fitting function.

9. The method according to claim 8, wherein:
    the fitting function is defined by $$\frac{D(\Delta, T_{2s})}{D_0} = 1 - (1-\alpha)\frac{\beta\frac{L_D}{\rho T_{2s}} + (1-\alpha)\left(\frac{L_D}{\Gamma\rho T_{2s}}\right)^2}{(1-\alpha) + \beta\frac{L_D}{\rho T_{2s}} + (1-\alpha)\left(\frac{L_D}{\Gamma\rho T_{2s}}\right)^2}$$

where $D_0$ is a bulk diffusion coefficient, $$\alpha = D(\infty)/D_0, \beta = \frac{4}{9\sqrt{\pi}}, L_D = \sqrt{D_0\Delta}, \text{ and } \Gamma = L_M/\rho T_{2s},$$

where $L_M$ is a length scale characterizing a transition between a short-time and long-time diffusion limit.

10. The method according to claim 9, wherein:
    the at least one parameter comprises $D_0$, $\alpha$, and $\Gamma$.

11. The method according to claim 1, wherein:
    the processing the resulting data comprises solving $$M(q_i, \tau_j) = \Sigma_{k,l}f(T_{2,k}, D_l)e^{-q_i^2 D_l \Delta}e^{-\frac{\tau_j}{T_{2,k}}}$$

to obtain the distribution $f(T_2,D)$ where $M(q_i,\tau_j)$ is the resulting data, q is the encoding strength, and $\tau$ is the time in CPMG decay.

12. The method according to claim 11, wherein:
    the solving comprises using a fast Laplace inversion.

13. The method according to claim 11, wherein:
    the calculating a mean diffusion coefficient $\overline{D}(T_{2s})$ for each $T_2$ value comprises converting $T_2$ indices into $T_{2s}$ indices by relabeling the $T_2$ index as a $T_{2s}$ index utilizing $$\frac{1}{T_{2s}} = \frac{1}{T_2} - \frac{1}{T_{2b}}$$

where $T_{2b}$ is the $T_2$ value of bulk fluid in the porous medium.

14. The method according to claim 13, wherein:
the calculating a mean diffusion coefficient $\overline{D}(T_{2s})$ for each $T_2$ value further comprises calculating according to $$\overline{D}(\Delta, T_{2s}) = \frac{\Sigma_i f(T_{2s}, D_i) * D_i^2}{\Sigma_i f(T_{2s}, D_i) * D_i}.$$

15. The method according to claim 11, wherein:
the calculating a mean diffusion coefficient $\overline{D}(T_{2s})$ for each $T_2$ value further comprises calculating according to $$\overline{D}(\Delta, T_{2s}) = \sqrt{\frac{\Sigma_i f(T_{2s}, D_i) * D_i^2}{\Sigma_i f(T_{2s}, D_i)}}.$$

16. The method according to claim 11, wherein:
the calculating a mean diffusion coefficient $\overline{D}(T_{2s})$ for each $T_2$ value further comprises calculating according to $$\overline{D}(\Delta, T_{2s}) = \frac{\Sigma_i f(T_{2s}, D_i) * D_i}{\Sigma_i f(T_{2s}, D_i)}.$$

17. The method according to claim 11, wherein:
the calculating a $T_2$ distribution $g(T_{2s})$ comprises calculating according to $g(\Delta, T_{2s}) = \Sigma_{D_i} f_\Delta(T_{2s}, D_i)$.

18. The method according to claim 9, wherein:
the processing the resulting data comprises solving $$M(q_i, \tau_j) = \Sigma_{k,l} f(T_{2,k}, D_l) e^{-q_i^2 D_l \Delta} e^{-\frac{\tau_j}{T_{2,k}}}$$

using a fast Laplace inversion to obtain the distribution $f(T_2, D)$ where $M(q_i, \tau_j)$ is the resulting data, q is the encoding strength, and $\tau$ is the time in CPMG decay.

19. The method according to claim 9, wherein:
the calculating a mean diffusion coefficient $\overline{D}(T_{2s})$ for each $T_2$ value comprises converting $T_2$ indices into $T_{2s}$ indices by relabeling the $T_2$ index as a $T_{2s}$ index utilizing $$\frac{1}{T_{2s}} = \frac{1}{T_2} - \frac{1}{T_{2b}}$$

where $T_{2b}$ is the $T_2$ value of bulk fluid in the porous medium.

20. The method according to claim 19, wherein:
the calculating a mean diffusion coefficient $\overline{D}(T_{2s})$ for each $T_2$ value further comprises calculating according to $$\overline{D}(\Delta, T_{2s}) = \frac{\Sigma_i f(T_{2s}, D_i) * D_i^2}{\Sigma_i f(T_{2s}, D_i) * D_i}.$$

21. The method according to claim 19, wherein:
the calculating a mean diffusion coefficient $\overline{D}(T_{2s})$ for each $T_2$ value further comprises calculating according to $$\overline{D}(\Delta, T_{2s}) = \sqrt{\frac{\Sigma_i f(T_{2s}, D_i) * D_i^2}{\Sigma_i f(T_{2s}, D_i)}}.$$

22. The method according to claim 19, wherein:
the calculating a mean diffusion coefficient $\overline{D}(T_{2s})$ for each $T_2$ value further comprises calculating according to $$\overline{D}(\Delta, T_{2s}) = \frac{\Sigma_i f(T_{2s}, D_i) * D_i}{\Sigma_i f(T_{2s}, D_i)}.$$

23. The method according to claim 19, wherein:
the calculating a $T_2$ distribution $g(T_{2s})$ comprises calculating according to $g(\Delta, T_{2s}) = \Sigma_{D_i} f_\Delta(T_{2s}, D_i)$.

24. The method according to claim 1, wherein:
the repeating a)-d) multiple respective times comprises repeating a) multiple times and storing the acquired resulting data prior to the processing, the calculating a mean diffusion coefficient, and the calculating a $T_2$ distribution.

25. The method according to claim 1, further comprising:
displaying an indication of the determination of surface relaxivity (ρ).

26. The method according to claim 25, wherein:
the displaying comprises generating a log of surface relaxivity as a function of depth in a borehole.

27. A method of determining surface relaxivity of a porous medium, comprising:
(a) generating multiple nuclear magnetic resonance (NMR) diffusion editing—CPMG (Carr-Purcell-Meiboom-Gill) pulse sequences with a diffusion encoding time $\Delta$ that interact with the porous medium, and acquiring resulting data;
(b) processing, by a processor, the resulting data to obtain a distribution $f(T_2, D)$ for that $\Delta$;
(c) calculating, by a processor, a mean diffusion coefficient $\overline{D}(T_{2s})$ for each $T_2$ value, where $T_{2s}$ is the transverse relaxation time due to surface relaxation;
(d) calculating, by a processor, a $T_2$ distribution $g(T_{2s})$; and
(e) utilizing, by a processor, the calculated $T_2$ distribution and the calculated mean diffusion coefficient in order to generate a determination of surface relaxivity (ρ) by choosing values for the surface relaxivity and at least one parameter to cause a fitting function of the surface relaxivity and a parameter $\Gamma$ to approximate the average diffusion coefficient $\overline{D}(T_{2s})$, the fitting function is defined by $$\frac{D(\Delta, T_{2s})}{D_0} = 1 - (1-\alpha)\frac{\beta\frac{L_D}{\rho T_{2s}} + (1-\alpha)\left(\frac{L_D}{\Gamma T_{2s}}\right)^2}{(1-\alpha) + \beta\frac{L_D}{\rho T_{2s}} + (1-\alpha)\left(\frac{L_D}{\Gamma T_{2s}}\right)^2}$$

where $D_0$ is a bulk diffusion coefficient, $$\alpha = D(\infty)/D_0, \beta = \frac{4}{9\sqrt{\pi}}, L_D = \sqrt{D_0 \Delta}, \text{ and } \Gamma = L_M/\rho T_{2s},$$

where $L_M$ is a length scale characterizing a transition between a short-time and long-time diffusion limit.

28. The method according to claim 27, wherein:
   the processing the resulting data comprises solving $$M(q_i, \tau_j) = \Sigma_{k,l} f(T_{2,k}, D_l) e^{-q_i^2 D_l \Delta} e^{-\frac{\tau_j}{T_{2,k}}}$$

to obtain the distribution $f(T_2,D)$ where $M(q_i,\tau_j)$ is the resulting data, q is the encoding strength, and $\tau$ is the time in CPMG decay.

29. The method according to claim 28, wherein:
   the calculating a $T_2$ distribution $g(T_{2s})$ comprises calculating according to $g(\Delta,T_{2s}) = \Sigma_{D_i} f_\Delta(T_{2s}, D_i)$.

30. The method according to claim 27, further comprising:
   displaying an indication of the determination of surface relaxivity ($\rho$).

31. A method utilizing nuclear magnetic resonance (NMR) measurements to determine surface relaxivity of a porous medium, comprising:
   (a) generating multiple NMR diffusion editing pulse sequences for each of a plurality of diffusion encoding times $\Delta$ that interact with the porous medium, and acquiring resulting data;
   (b) processing, by a processor, the resulting data to obtain mean diffusion coefficient $\overline{D}(T_{2s})$ for each $T_2$ value of each of the plurality of encoding times $\Delta$, where $T_{2s}$ is the transverse relaxation time due to surface relaxation, and to obtain $T_2$ distributions $g(T_{2s})$; and
   (c) utilizing, by a processor, respective calculated $T_2$ distributions and respective calculated mean diffusion coefficients in a data-fitting error minimization procedure in order to generate a determination of surface relaxivity ($\rho$), where the data-fitting error minimization procedure utilizes a fitting function with a parameter that permits the length scale characterizing the transition between the short-time and long-time diffusion limit ($L_M$) to scale with pore size.

32. The method according to claim 31, wherein:
   the data-fitting error minimization comprises choosing values for the surface relaxivity and at least one parameter to cause a fitting function of the surface relaxivity and the at least one parameter to closely approximate a data set of the average diffusion coefficients $\overline{D}(\Delta,T_{2s})$.

33. The method according to claim 32, wherein:
   the data-fitting error minimization comprises utilizing a logarithmic error.

34. The method according to claim 33, wherein:
   the logarithmic error is defined according to $\text{err} = \Sigma_{\Delta,T_{2s}} \{g(\Delta,T_{2s}) * [\log D_{fit}(\Delta,T_{2s}) - \log \overline{D}(\Delta,T_{2s})]\}^2$, where $D_{fit}(\Delta,T_{2s})$ is the fitting function.

35. The method according to claim 31, wherein:
   the fitting function is defined by $$\frac{D(\Delta, T_{2s})}{D_0} = 1 - (1-\alpha) \frac{\beta \frac{L_D}{\rho T_{2s}} + (1-\alpha)\left(\frac{L_D}{\Gamma \rho T_{2s}}\right)^2}{(1-\alpha) + \beta \frac{L_D}{\rho T_{2s}} + (1-\alpha)\left(\frac{L_D}{\Gamma \rho T_{2s}}\right)^2}$$

where $D_0$ is a bulk diffusion coefficient, $$\alpha = D(\infty)/D_0, \beta = \frac{4}{9\sqrt{\pi}}, L_D = \sqrt{D_0 \Delta}, \text{ and } \Gamma = L_M/\rho T_{2s},$$

where $L_M$ is a length scale characterizing a transition between a short-time and long-time diffusion limit.

36. The method according to claim 35, wherein:
   the at least one parameter comprises $D_0$, $\alpha$, and $\Gamma$.

37. The method according to claim 31, wherein:
   the processing the resulting data comprises solving $$M(q_i, \tau_j) = \Sigma_{k,l} f(T_{2,k}, D_l) e^{-q_i^2 D_l \Delta} e^{-\frac{\tau_j}{T_{2,k}}}$$

to obtain the distribution $f(T_2,D)$ where $M(q_i,\tau_j)$ is the resulting data, q is the encoding strength, and $\tau$ is the time in CPMG decay.

38. The method according to claim 37, wherein:
   the solving comprises using a fast Laplace inversion.

39. The method according to claim 31, further comprising:
   displaying an indication of the determination of surface relaxivity ($\rho$).

40. The method according to claim 39, wherein:
   the displaying comprises generating a log of surface relaxivity as a function of depth in a borehole.

41. A method of determining surface relaxivity of a porous medium, comprising:
   generating multiple nuclear magnetic resonance (NMR) diffusion editing pulse sequences having gradient pulses for diffusion editing separated for each of a plurality of diffusion encoding times $\Delta$, wherein said multiple NMR diffusion editing pulse sequences that interact with the porous medium, and acquiring resulting data; and
   without utilizing non-NMR measurements, using a processor to fit a function relating the surface relaxivity to NMR diffusion coefficients and diffusion lengths to diffusion coefficients calculated from the resulting data in order to obtain a surface relaxivity determination for the porous medium.

42. The method according to claim 41, wherein:
   the function is defined by $$\frac{D(\Delta, T_{2s})}{D_0} = 1 - (1-\alpha) \frac{\beta \frac{L_D}{\rho T_{2s}} + (1-\alpha)\left(\frac{L_D}{\Gamma \rho T_{2s}}\right)^2}{(1-\alpha) + \beta \frac{L_D}{\rho T_{2s}} + (1-\alpha)\left(\frac{L_D}{\Gamma \rho T_{2s}}\right)^2}$$

where $\rho$ is the surface relaxivity, $D_0$ is a bulk diffusion coefficient, $$\alpha = D(\infty)/D_0, \beta = \frac{4}{9\sqrt{\pi}}, L_D = \sqrt{D_0 \Delta}$$

is a diffusion length, and $\Gamma = L_M/\rho T_{2s}$, where $L_M$ is a length scale characterizing a transition between a short-time and long-time diffusion limit.

43. The method according to claim 41, further comprising:
   displaying an indication of the determination of surface relaxivity ($\rho$).

44. A nuclear magnetic resonance (NMR) system comprising:
- a coil for applying a NMR pulse sequence to a substance;
- a NMR transmitter coupled to the coil;
- a processor; and
- a memory storing instructions executable by the processor to
  - apply multiple nuclear magnetic resonance (NMR) diffusion editing Carr-Purcell-Meiboom-Gill (CPMG) pulse sequences to the porous medium, wherein the diffusion editing CPMG pulse sequences have gradient pulses for diffusion editing separated by a diffusion encoding time $\Delta$;
  - receive NMR data generated by the pulse sequences;
  - process the received NMR data to obtain a distribution $f(T_2,D)$ for the diffusion encoding time $\Delta$;
  - repeat the applying, the receiving, and the processing at least one time for pulse sequences having different respective diffusion encoding times $\Delta$ to obtain respective distributions $f(T_2,D)$ corresponding respectively to the different diffusion encoding times $\Delta$; and
  - utilize the respectively obtained distributions $f(T_2,D)$ together to generate a surface relaxivity ($\rho$) determination.

45. The NMR system of claim 44, wherein the NMR system is part of a wellbore tool for investigating formations.

* * * * *